United States Patent [19]
Phillips et al.

[11] Patent Number: 5,509,920
[45] Date of Patent: Apr. 23, 1996

[54] SURGICAL HEMOSTATIC CLIP

[75] Inventors: Paul J. Phillips, Middlebury; Mark S. Peyser, Monroe; John Webster, Cromwell, all of Conn.

[73] Assignee: United States Surgical Corporation, Norwalk, Conn.

[21] Appl. No.: 283,949

[22] Filed: Aug. 1, 1994

Related U.S. Application Data

[63] Continuation of Ser. No. 48,467, Apr. 16, 1993, abandoned.

[51] Int. Cl.$^6$ .................................................. A61B 17/04
[52] U.S. Cl. .......................... 606/157; 606/158; 227/902
[58] Field of Search .......................... 606/151, 157–158, 606/142–143; 227/902

[56] References Cited

U.S. PATENT DOCUMENTS

| | | |
|---|---|---|
| 3,006,344 | 10/1961 | Vogelfanger . |
| 3,175,556 | 3/1965 | Wood et al. . |
| 3,363,628 | 1/1968 | Wood . |
| 3,867,944 | 2/1975 | Samuels . |
| 3,874,042 | 4/1975 | Eddleman et al. ........................ 606/151 |
| 4,064,881 | 12/1977 | Meredith ................................... 606/157 |
| 4,146,130 | 3/1979 | Samuels et al. ........................... 206/340 |
| 4,188,953 | 2/1980 | Klieman et al. . |
| 4,278,091 | 7/1981 | Borzone . |
| 4,346,869 | 8/1982 | MacNeill . |
| 4,394,864 | 7/1983 | Sandhaus . |
| 4,407,286 | 10/1983 | Noiles et al. . |
| 4,412,539 | 11/1983 | Jarvik . |
| 4,414,721 | 11/1983 | Hufnagel . |
| 4,449,530 | 5/1984 | Bendel et al. . |
| 4,487,205 | 12/1984 | Di Giovanni et al. ................ 606/158 |
| 4,489,875 | 12/1984 | Crawford et al. . |
| 4,519,392 | 5/1985 | Lingua . |
| 4,531,522 | 7/1985 | Bedi et al. . |
| 4,570,623 | 2/1986 | Ellison et al. . |
| 4,624,254 | 11/1986 | McGarry et al. . |
| 4,702,247 | 10/1987 | Blake, III et al. . |
| 4,796,627 | 1/1989 | Tucker . |
| 4,799,481 | 1/1989 | Transue et al. . |
| 4,844,066 | 7/1989 | Stein . |
| 4,971,198 | 11/1990 | Mericle ................................... 206/339 |
| 4,976,722 | 12/1990 | Failla ...................................... 606/157 |
| 4,979,950 | 12/1990 | Transue et al. . |
| 5,171,250 | 12/1992 | Yoon . |
| 5,171,252 | 12/1992 | Friedland . |
| 5,171,253 | 12/1992 | Klieman . |
| 5,201,746 | 4/1993 | Shichman ............................... 606/151 |

FOREIGN PATENT DOCUMENTS

| | | |
|---|---|---|
| 853499 | 10/1952 | Germany . |
| 8522122 | 10/1985 | Germany . |

*Primary Examiner*—Gary Jackson

[57] ABSTRACT

A hemostatic clip for application to body tissue is disclosed which includes opposed leg portions connected by a bail portion with each leg portion having a tissue contacting surface defined thereon. A pair of projections and a pair of recessed areas are defined on each tissue contacting surface and are disposed in an alternating arrangement such that the movement inhibiting structures on one leg portion are in juxtaposed alignment with those on the opposed leg portion.

29 Claims, 6 Drawing Sheets

SURGICAL HEMOSTATIC CLIP

This is a continuation of application Ser. No. 08/048,467 filed on Apr. 16, 1993 now abandoned.

BACKGROUND OF THE INVENTION

1. Field of the Invention

This invention relates to surgical clips, and more particularly to hemostatic surgical clips for application to blood vessels or body tissue.

2. Description of Related Art

Ligation or occlusion of veins, arteries or blood vessels has been a necessary part of surgical procedures for many years. Typically, a severed blood vessel requires closure on both sides of a severance site before actual cutting takes place. In the past, surgeons used thread or suture material to tie a blood vessel prior to severing the vessel. This procedure was often time consuming and required great dexterity on the part of the surgeon to properly close the vessel. In many instances, the assistance of a nurse or attending surgeon was necessary to perform this procedure.

The advent of surgical clips and clip appliers has greatly enhanced the art of vessel occlusion. Surgical clips are now commonly used for vessel ligation and occlusion. Examples of surgical hemostatic clips are described in U.S. Pat. Nos. 5,171,253; 5,171,252; 5,100,420; 5,084,057; 4,971,198; 4,844,066; 4,799,481; 4,702,247; 4,414,721; 4,188,953; 4,146,130; 3,867,944; and 3,363,628.

Many factors are critical to the design of a surgical hemostatic clip. For example, it is imperative that the clip does not slip or become dislodged from a blood vessel after it has been applied. If the clip is not securely positioned, blood may begin flowing into the surgical site through the unclamped vessel. This serves to delay the operation while the surgeon locates and reclamps the vessel. Depending upon the type and location of the surgery, repairing the vessel may be difficult.

Another consideration is that a surgical hemostatic clip should be designed to fully and completely close about a vein, artery, or blood vessel and completely stop the flow therethrough. A clip which does not completely occlude the flow of blood may be unsuitable for its intended function.

Generally, surgical hemostatic clips are U-shaped or V-shaped in configuration and define a pair of legs joined at one end by an apex or crown and spaced apart at the opposed ends to define an opening therebetween. The inside surfaces of the clip legs may be constructed in a manner to improve the occluding functions of the clip as well as to restrict longitudinal and transverse dislocation of the clip after it has been applied to the target blood vessel. An example of a clip having such a construction is described in U.S. Pat. No. 4,976,722 which issued to Failla. This clip includes an elongated groove defined in one of the legs thereof with a correspondingly configured tongue depending from the opposed leg thereof. Transverse grooves are formed across the tongue and groove for enhanced gripping during application of the clip.

An improved surgical hemostatic clip is needed however, to provide optimum vessel occlusion and clip retention on tissue during a surgical procedure. Accordingly, it is an object of the subject invention to provide a surgical hemostatic clip having improved movement inhibiting construction intended to inhibit both longitudinal and transverse dislocation of the clip relative to the tissue to which it is applied.

SUMMARY OF THE INVENTION

A hemostatic clip is provided for application to body tissue which comprises a clip body defining first and second opposed leg portions and a connecting bail portion. A tissue contacting surface is defined on each of the leg portions, with the tissue contacting surface of the first leg portion having a plurality of spaced apart projections provided thereon, and the tissue contacting surface of the second leg portion having a plurality of spaced apart recessed areas provided therein in juxtaposed alignment with the projections for respective reception of the projections during the application of the hemostatic clip so as to inhibit dislocation of the clip relative to the body tissue to which it is applied.

In a preferred embodiment of the surgical hemostatic clip of the subject invention, the tissue contacting surface defined on each of the opposed leg portions of the clip includes a plurality of movement inhibiting structures. The movement inhibiting structures include a pair of projections and a pair of recessed areas disposed equidistant from one another in an alternating arrangement. Preferably, the distal-most movement inhibiting structure provided on the first leg is a projection while the distal-most movement inhibiting structure provided on the second leg is a recessed area, such that the plurality of movement inhibiting structures on the first leg are in juxtaposed alignment with the plurality of movement inhibiting structures on the second leg to facilitate enhanced engagement of tissue therebetween during application of the surgical hemostatic clip to a tubular blood vessel.

Further features of the subject invention will become more readily apparent to those having ordinary skill in the art to which this invention appertains from the following detailed description of the invention taken in conjunction with the drawings.

BRIEF DESCRIPTION OF THE DRAWINGS

In order that those skilled in the art to which this invention appertains may understand how to make and use the same, a detailed description of the construction thereof in accordance with a preferred embodiment of the subject invention will follow, referring by numerals to the accompanying drawings wherein.

DETAILED DESCRIPTION OF THE PREFERRED EMBODIMENTS

The surgical hemostatic clip of the subject invention is applied to body tissue by an appropriate surgical clip applying apparatus. A surgical clip applying apparatus generally has structure to position the clip relative to the tissue to which it will be applied, and a mechanism to deform the clip, usually by bending the clip at its apex so that the legs thereof close off the blood vessel. Illustrative surgical instruments suitable for use in the application of the surgical hemostatic clips of the subject invention are described in U.S. Pat. No. 4,509,518 to McGarry et al., U.S. Pat. Nos. 5,084,057 and 5,100,420 to Green et al., the disclosures of which are herein incorporated by reference.

Figure 1:
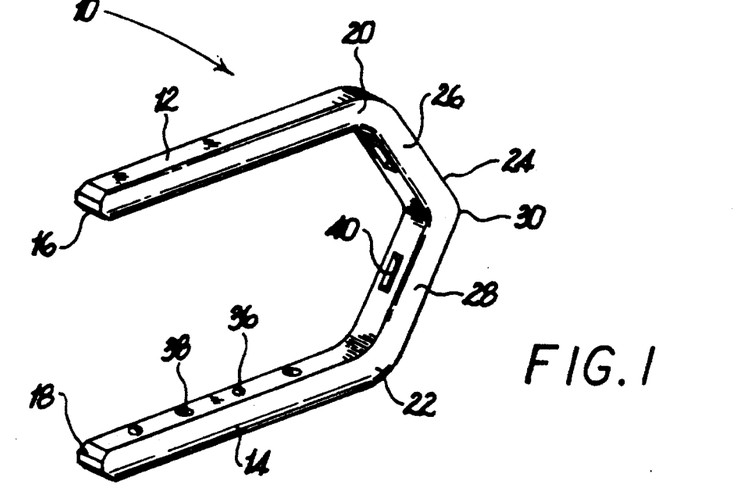
FIG. 1 is a perspective view of a surgical hemostatic clip in accordance with a preferred embodiment of the subject invention.

Referring now to FIG. 1, the surgical hemostatic clip 10 of the subject invention includes a pair of opposed leg portions 12 and 14 each having respective distal end regions 16 and 18, and respective proximal end regions 20 and 22. The proximal end regions 20 and 22 of each of the leg portions of hemostatic clip 10 are connected to respective ends of a bail portion 24. The bail portion 24 of hemostatic clip 10 is defined by angled bail sections 26 and 28 which culminate in an apex 30 to form the generally V-shaped or U-shaped configuration of hemostatic clip 10. Each of the leg portions 12 and 14 of hemostatic clip 10 define a respective tissue contacting surface between which tissue is clamped during application of the surgical hemostatic clip 10 to a tubular blood vessel. Leg portion 12 defines tissue contacting surface 32, while leg portion 14 defines tissue contacting surface 34.

A plurality of movement inhibiting structures are formed on each of the tissue contacting surfaces 32 and 34 for cooperatively inhibiting dislocation of the hemostatic clip 10 with respect to the body tissue to which it is applied. In the embodiment of FIG. 1, the movement inhibiting structures include a plurality of convex protuberances 36 and a plurality of concave recessed areas 38 which are disposed in an alternating pattern on each of the opposed tissue contacting surfaces 32 and 34 of hemostatic clip 10. Those having ordinary skill in the art to which the subject invention appertains will appreciate that other alternative structures may be utilized therein. The arrangement of the movement inhibiting structures is such that a protuberance located on a tissue contacting surface of one of the leg portions of the clip will be in juxtaposed alignment with a recessed area defined on a tissue contacting surface of the opposite leg portion of the clip such that upon application of the clip to body tissue each of the protuberances will urge tissue into a corresponding recessed area.

Figure 2:
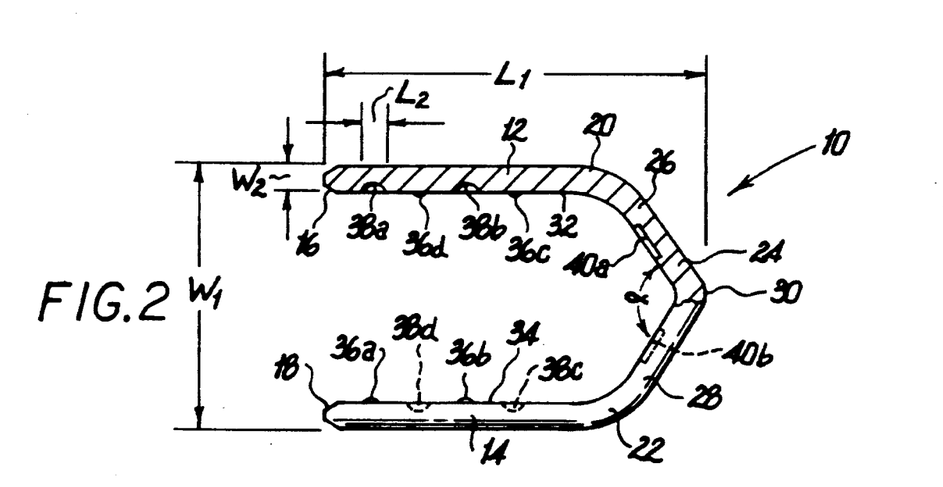
FIG. 2 is a side elevational view, in partial cross-section, of the surgical hemostatic clip of FIG. 1.
Figure 3:
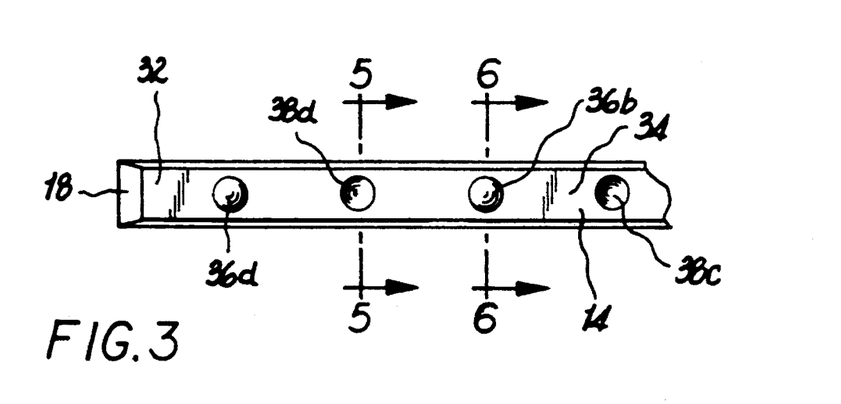
FIG. 3 is a partial plan view of the tissue contacting surface of one of the leg portions of the surgical hemostatic clip of FIG. 1.
Figure 4:
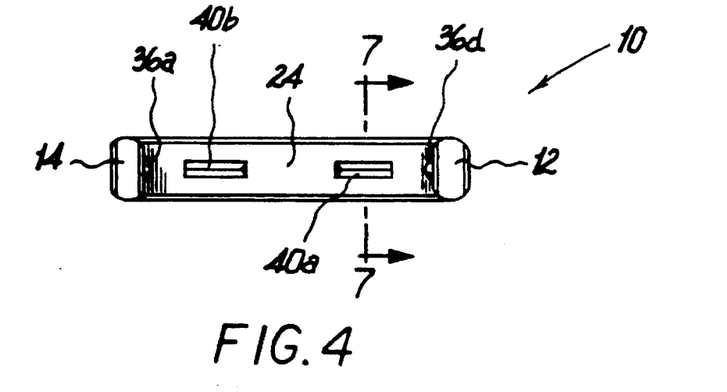
FIG. 4 is a front elevational view of the surgical hemostatic clip of FIG. 1.
Figure 5:
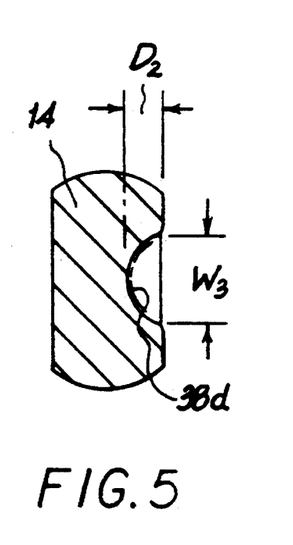
FIG. 5 is a cross-sectional view taken along line 5—5 of FIG. 3.
Figure 6:
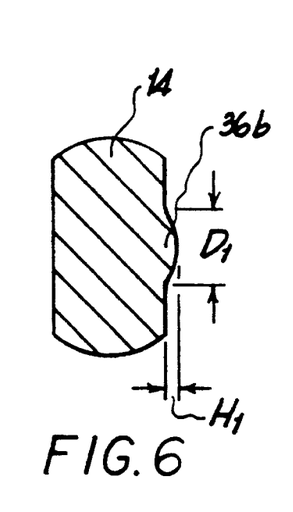
FIG. 6 is a cross-sectional view taken along line 6—6 of FIG. 3.

Turning to FIGS. 2 and 3, the movement inhibiting structures defined on each of the tissue contacting surfaces 32 and 34 includes first through fourth structures, with the first structure being the distal-most member of the group and the fourth structure being the proximal-most member of the group. The first movement inhibiting structure defined on tissue contacting surface 32 of leg portion 12 adjacent the distal end region 16 thereof is a concave recessed area 38a. The remaining movement inhibiting structures defined on tissue contacting surface 32, in distal-to-proximal order, include convex protuberance 36d, concave recessed area 38b, and convex protuberance 36c. The first movement inhibiting structure defined on tissue contacting surface 34 of leg portion 14 adjacent the distal end region 18 thereof is a convex protuberance 36a. The remaining movement inhibiting structures defined on tissue contacting surface 34, in distal-to-proximal order, include concave recessed area 38d, convex protuberance 36b, and concave recessed area 38c.

Figure 7:
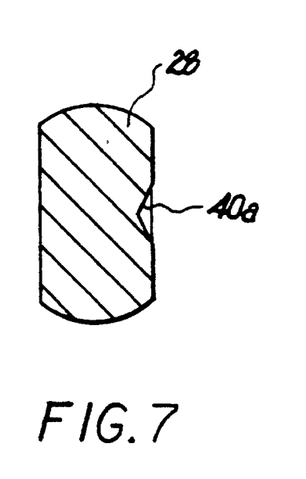
FIG. 7 is a cross-sectional view taken along line 7—7 of FIG. 4.

In addition to the plurality of movement inhibiting structures defined on the respective tissue contacting surfaces 32 and 34 of leg portions 12 and 14, a pair of tissue expansion notches 40a and 40b are defined respectively on the inner surfaces of the angled bail sections 26 and 28 of the bail portion 24 of hemostatic clip 10. As best seen in FIG. 7, expansion notches 40a and 40b have a substantially V-shaped cross-section which permits tissue exudation during the application of hemostatic clip 10 to a tissue. The exudation of tissue into notches 40a and 40b further inhibits movement of the hemostatic clip 10 relative to the vessel to which it is applied.

Referring to FIGS. 2–6, the surgical hemostatic clip 10 of the subject invention may be of any dimension suitable for application to body tissue. Preferably, the length $L_1$ of the clip is about 0.3 inches, the width $W_1$ of the clip is from about 0.2 to about 0.25 inches, while the width $W_2$ of the clip's legs is from about 0.03 to about 0.04 inches. The diameter $D_1$ of each of the protuberances 36a–36d is from about 0.01 inches to about 0.02 inches, while their height $H_1$ is about 0.002 inches. The depth $D_2$ of each of the recessed areas 38a–38d is from about 0.005 to about 0.007 inches, while their length $L_2$ is from about 0.03 to about 0.04 inches, and their width $W_3$ is from about 0.01 to about 0.03 inches. The increased length at the recessed areas 38a–38d relative to the diameter of protuberances 36a–36d helps to ensure alignment thereof when clip 10 is formed on tissue. The angle α formed between the angled bail sections 26 and 28 of bail portion 24 is preferably from about 120° to about 140°. One having ordinary skill in the art to which the subject invention appertains will recognize that other dimensions can also be used.

The movement inhibiting structures of the present invention may be formed in clip 10 by fixturing the clip and applying an appropriate stamping force to the interior and exterior faces of leg portions 12 and 14 to form recesses on the force-receiving faces. Corresponding protuberances may appear on the opposite face and/or the clip material may "swage out" along the periphery of the clip to a limited degree. Alternatively, movement inhibiting structures may be formed by machining clip 10 or other known metal or polymer processing techniques. For example, clip 10 may be molded with movement inhibiting structures formed therein.

Figure 8:
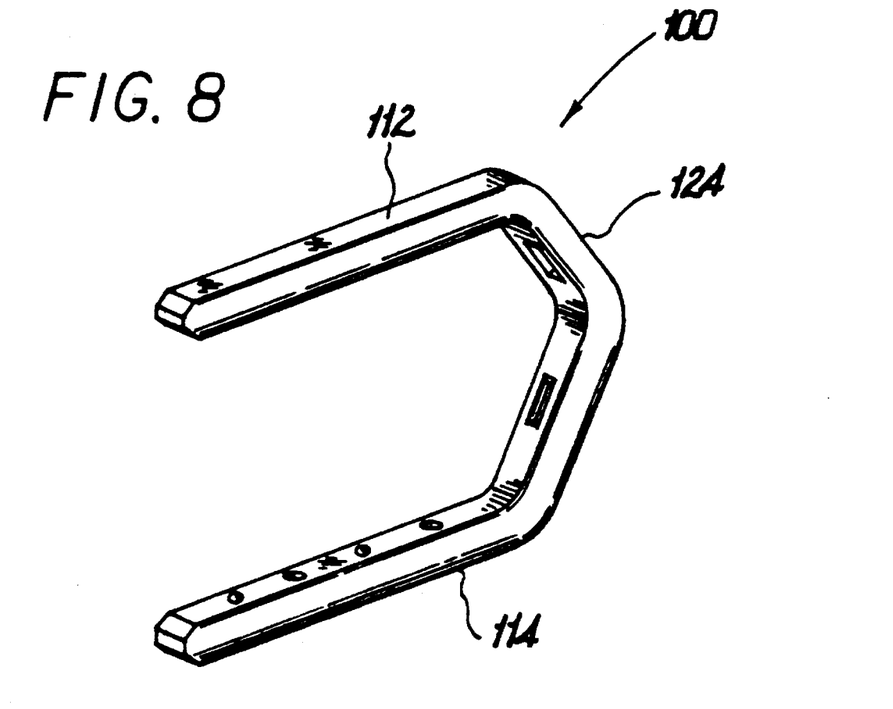
FIG. 8 is a perspective view of another surgical hemostatic clip in accordance with the subject invention.
Figure 9:
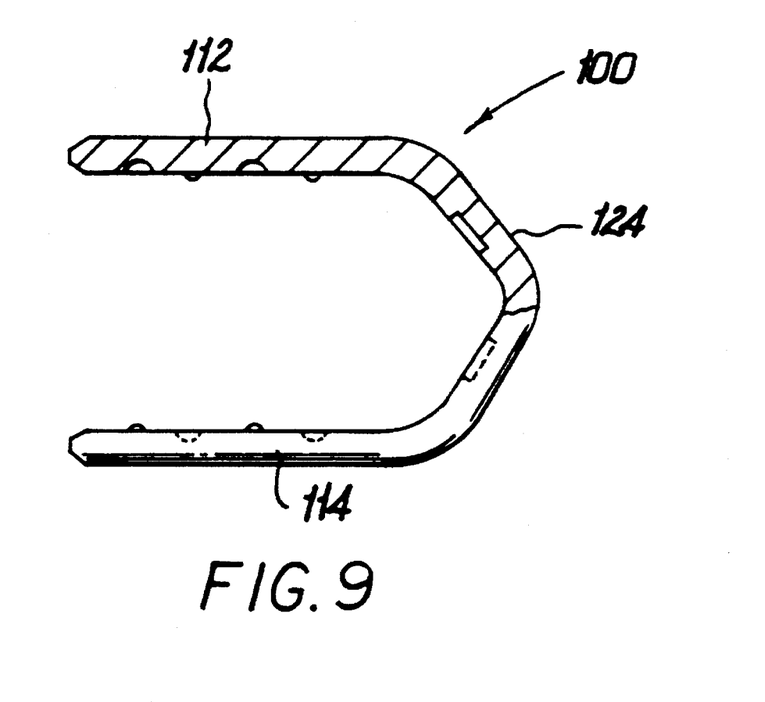
FIG. 9 is a side elevational view, in partial cross-section, of the surgical hemostatic clip of FIG. 8.

Turning to FIGS. 8 and 9, another surgical hemostatic clip in accordance with a preferred embodiment of the subject invention is illustrated and is designated generally by reference numeral 100. The construction of surgical hemostatic clip 100 is substantially similar to that of the surgical hemostatic clip 10 of the previous embodiment except that the opposed leg portions 112 and 114 thereof are connected by a substantially arcuate bail portion 124. Accordingly, surgical hemostatic clip 100 defines a substantially U-shaped configuration rather than the substantially V-shaped configuration of surgical hemostatic clip 10.

The surgical hemostatic clip 10 of the subject invention can be fabricated from any surgically suitable biocompatible material including, inter alia, stainless steel, titanium, and tantalum, as well as plastic materials including bioabsorbable polymers.

Figure 10:
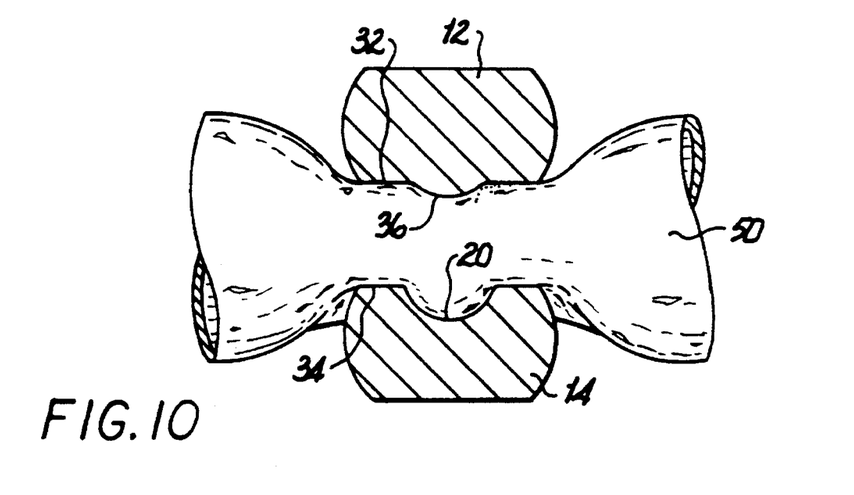
FIG. 10 is a cross-sectional view of the surgical hemostatic clip of the subject invention applied to a tubular blood vessel.
Figure 11:
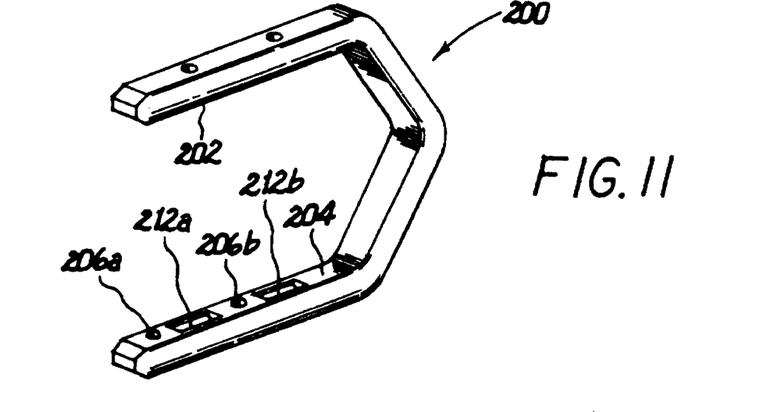
FIG. 11 is a perspective view of another surgical hemostatic clip in accordance with a preferred embodiment of the subject invention.

Referring to FIG. 10, in operation the surgical hemostatic clip 10 of the subject invention may be applied to a tubular organic structure such as blood vessel 50 during a surgical ligation procedure. Once applied to blood vessel 50, each of the projections 38 defined on the tissue contacting surfaces of hemostatic clip 10 will urge the tissue of the walls of blood vessel 50 into a corresponding juxtaposed recessed area 38 so as to inhibit longitudinal and transverse dislocation of the surgical hemostatic clip 10 relative to the tubular blood vessel 50. Once hemostatic clips have been applied at two spaced apart locations along the length of blood vessel 50 to close the tubular pathway, the vessel may be ligated at a location intermediate the two clips.

Figure 12:
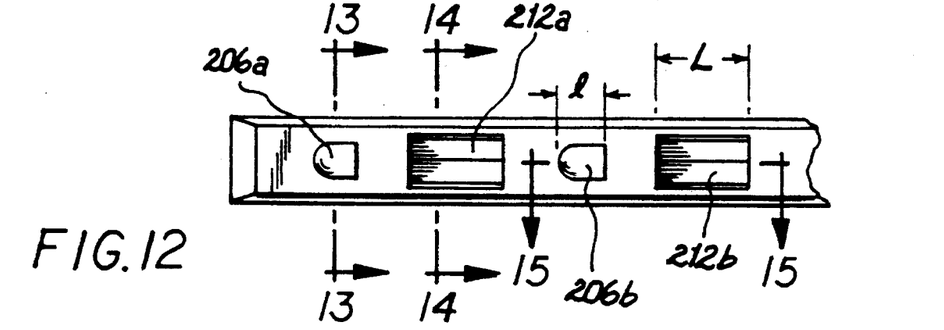
FIG. 12 is a plan view of a tissue contacting surface defined on a leg portion of the clip of FIG. 11.
Figures 13, 14, 15:
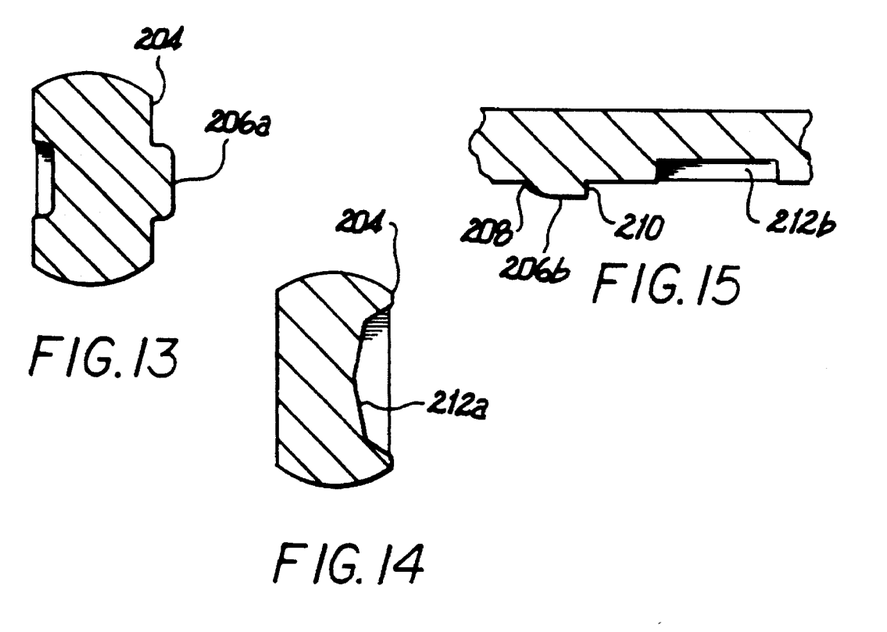
FIG. 13 is a cross-sectional view taken along line 13—13 of FIG. 12.
FIG. 14 is a cross-sectional view taken along line 14—14 of FIG. 12.
FIG. 15 is a cross-sectional view taken along line 15—15 of FIG. 12.
Figure 16:
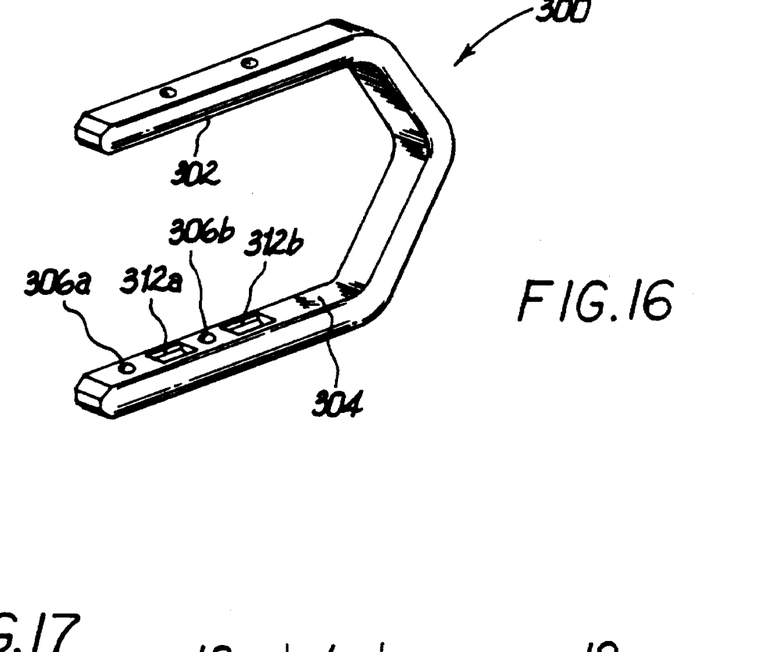
FIG. 16 is a perspective view of yet another surgical hemostatic clip in accordance with a preferred embodiment of the subject invention.

Referring now to FIGS. 11–15, another surgical hemostatic clip in accordance with a preferred embodiment of the subject invention is illustrated and is designated generally by reference numeral 200. Surgical clip 200 is similar to surgical clip 10 with the exception of the configuration of the protuberance and the corresponding recessed areas. In particular, the opposed tissue contacting surfaces 202 and 204 of clip 200 are provided with a plurality of protuberances 206a–206d each having a substantially polygonal cross-sectional configuration which is shown in FIG. 13. Each of the protuberances 206a–206d are also formed with a ramped leading edge portion defining an arcuate surface 208 and an upstanding trailing surface 210 as illustrated in FIG. 15. These surfaces serve to further inhibit longitudinal dislocation of clip 200 when it is applied to tissue. The opposed tissue contacting surfaces 202 and 204 of clip 200 are also provided with a plurality of elongated recessed areas 212a–212d, each having a substantially polygonal cross-sectional configuration which is best seen in FIG. 14. Preferably, as shown in FIG. 12, the length "L" of each of the plurality of recessed areas 212a–212d of surgical clip 200 exceeds the lengthwise dimension "l" of the major axis of each of the plurality of protuberances 206a–206d thereof by a factor of two to promote maximum tissue engagement during use.

Figure 17:
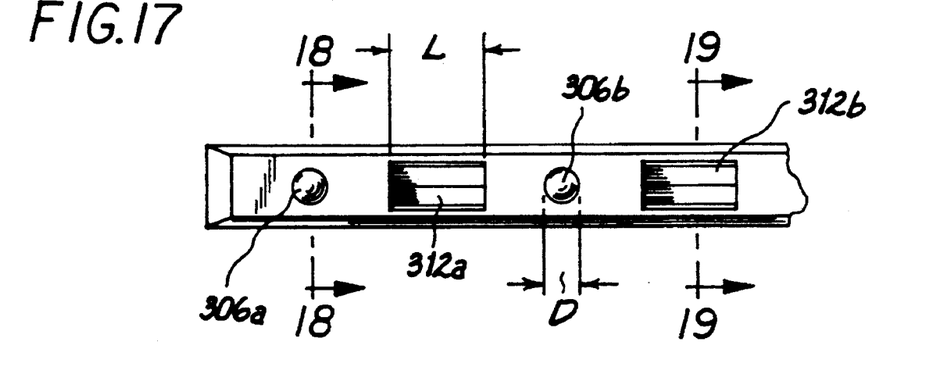
FIG. 17 is a plan view of a tissue contacting surface defined on a leg portion of the clip of FIG. 16.
Figure 18:
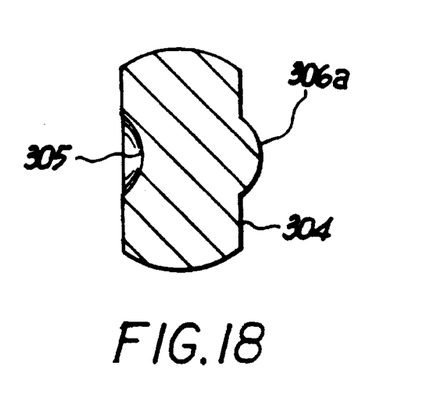
FIG. 18 is a cross-sectional view taken along line 18—18 of FIG. 17.
Figure 19:
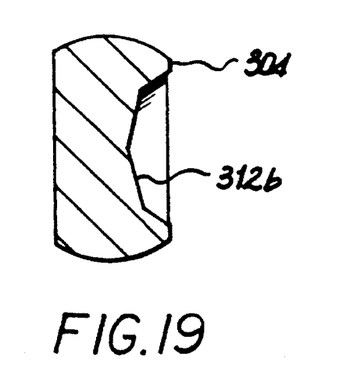
FIG. 19 is a cross-sectional view taken along line 18—18 of FIG. 17.
Figure 20:
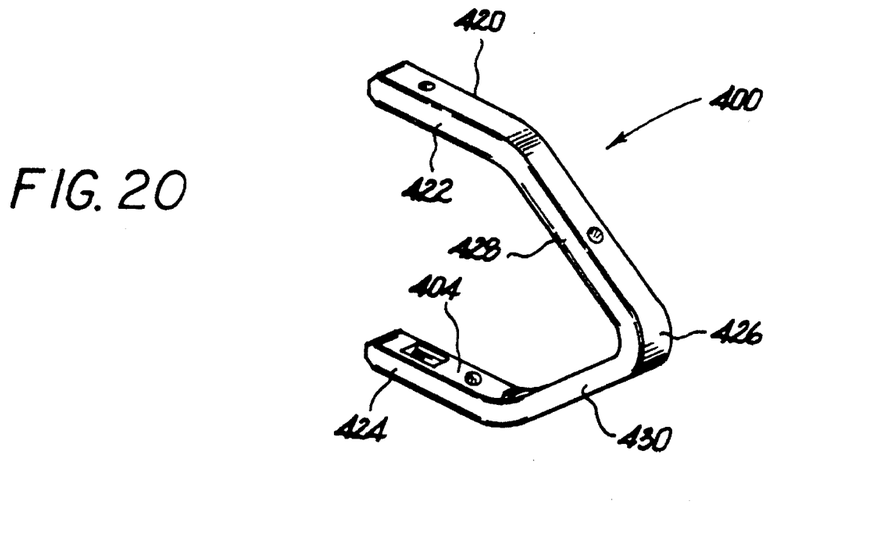
FIG. 20 is a perspective view of still another hemostatic surgical clip in accordance with a preferred embodiment of the subject invention.

Turning to FIGS. 16–19, yet another surgical hemostatic clip in accordance with a preferred embodiment of the subject invention is illustrated and is designated generally by reference numeral 300. Hemostatic clip 300 is substantially similar to clip 200 except that the plurality of protuberances 306a–306d which are associated therewith are substantially hemispherical in configuration. As discussed briefly above, during the stamping process in which the protuberances 306a–306d are formed, a correspondingly shaped recess is formed in the outer surface 305 of the clip. This stamp formed recess is illustrated in FIG. 18 and is designated by reference numeral 307. Preferably, as shown in FIG. 17, the lengthwise dimension "L" of each of the plurality of recessed areas 312a–312d of surgical clip 300 exceeds the diameter "D" of each of the plurality of protuberances 306a–306d thereof by a factor of two to maximize tissue engagement during use.

Figure 21:
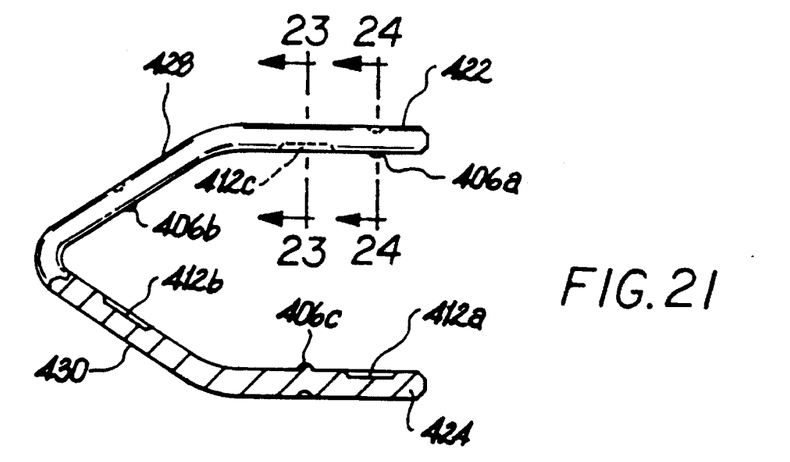
FIG. 21 is a side elevational view in partial cross-section of the clip of FIG. 20.
Figure 22:
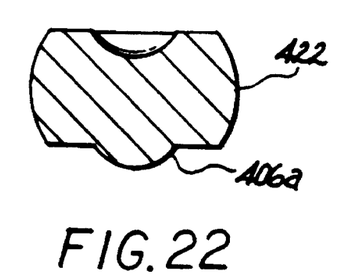
FIG. 22 is a cross-sectional view taken along line 22–22 of FIG. 21.
Figure 23:
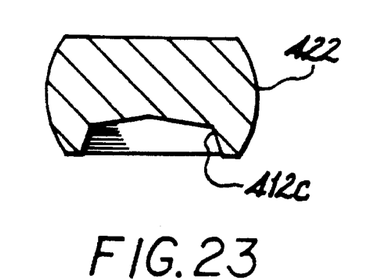
FIG. 23 is a cross-sectional view taken along line 23–23 of FIG. 21.

Turning now to FIGS. 20–23, still another embodiment of the surgical hemostatic clip of the subject invention is illustrated and is designated generally by reference numeral 400. Surgical clip 400 is defined by a clip body 420 having opposed leg portions 422 and 424 connected to each other by a V-shaped bail portion 426. Bail portion 426 is further defined by diverging bail legs 428 and 430. The configuration of the movement inhibiting structures provided on the opposed tissue contacting surfaces 402 and 404 of surgical clip 400 correspond substantially to those described previously in connection with hemostatic surgical clip 300, i.e. the protuberances 406a–406c are substantially hemispherical in configuration as shown in FIG. 22, and the recessed areas 412a–412c have a substantially polygonal cross-sectional configuration as shown in FIG. 23. However, in this embodiment, the arrangement and quantity of the movement inhibiting structures differs. In particular, each tissue contacting surface of surgical hemostatic clip 400 is provided with three movement inhibiting structures disposed in an alternating arrangement. As best seen in FIG. 21, two of the structures are defined on each of the leg portions 422 and 424 of the surgical clip 400, while a third movement inhibiting structure is provided on each of the bail legs 428 and 430 thereof.

Although the hemostatic surgical clip of the subject invention has been described with respect to a preferred embodiment, it is apparent that changes or modifications made be made thereto without departing from the spirit or scope of the invention as defined by the appended claims.

What is claimed is:

1. A hemostatic clip for application to body tissue comprising:

a unitary clip body defining first and second opposed elongated leg portions and a connecting bail portion, each of said first and second leg portions having opposed side walls defining opposing boundaries and an elongated tissue contacting surface defined thereon, said tissue contacting surface of said first leg portion having a plurality of longitudinally spaced apart protuberances provided thereon and disposed within said opposing boundaries defined by said opposed side walls of said first leg portion, said tissue contacting surface of said second leg portion having a plurality of longitudinally spaced apart recessed areas provided therein and disposed within said opposing boundaries defined by said opposed side walls of said second leg portion in juxtaposed alignment with said protuberances, said protuberances being dimensioned and configured to urge body tissue into said recessed areas during the application of said hemostatic clip so as to inhibit longitudinal and transverse movement of said hemostatic clip relative to the body tissue to which it is applied without causing trauma thereto, wherein each recessed area has a lengthwise dimension which exceeds a lengthwise dimension of each protuberance by a factor of at least two.

2. A hemostatic clip as recited in claim 1, wherein said plurality of protuberances are each substantially convex in configuration.

3. A hemostatic clip as recited in claim 1, wherein said plurality of recessed areas are each substantially concave in configuration.

4. A hemostatic clip as recited in claim 1, further comprising means associated with an inner surface of said bail portion for permitting tissue exudation during application of said hemostatic clip.

5. A hemostatic clip as recited in claim 4, wherein said means for permitting tissue exudation comprises a pair of spaced apart notches each having a substantially V-shaped cross-sectional configuration.

6. A hemostatic clip as recited in claim 1, wherein said plurality of protuberances each have a ramped leading edge portion.

7. A hemostatic clip as recited in claim 1, wherein said plurality of protuberances each have a substantially polygonal cross-sectional configuration.

8. A hemostatic clip as recited in claim 1, wherein said plurality of recessed areas each have a substantially polygonal cross-sectional configuration.

9. A hemostatic clip as recited in claim 1, wherein each of said plurality of protuberances has a lengthwise dimension of about between 0.01 inches and 0.02 inches.

10. A hemostatic clip as recited in claim 1, wherein each of said plurality of recessed areas has a lengthwise dimension of about between 0.02 inches and 0.04 inches.

11. A hemostatic clip as recited in claim 1, wherein said clip is fabricated from a material selected from the group consisting of stainless steel, tantalum, and titanium.

12. A hemostatic clip as recited in claim 1, wherein said plurality of spaced apart recessed areas are generally polyhedral in configuration.

13. A hemostatic clip as recited in claim 1, wherein said plurality of spaced apart recessed areas are generally spherical in configuration.

14. A hemostatic clip as recited in claim 1, wherein said opposed side walls of each leg portion are arcuate in configuration.

15. A hemostatic clip for application to body tissue comprising:

a unitary clip body defining first and second opposed elongated leg portions having respective proximal and distal ends with the proximal ends thereof connected by a bail portion, each of said first and second leg portions having opposed side walls defining opposing boundaries and a tissue contacting surface defined thereon which includes a plurality of structures disposed within said opposing boundaries defined by said first and second leg portions, said structures on each of said leg portions including a pair of projections and a pair of recessed areas disposed in an alternating arrangement, the distal-most structure provided on said first leg being a projection and the distal-most structure provided on said second leg being a recessed area, such that said plurality of structures on said first leg are in juxtaposed alignment with said plurality of structures on said second leg, said projections being dimensioned and configured to urge body tissue into said recessed areas during the application of said hemostatic clip so as to inhibit longitudinal and transverse movement of said hemostatic clip relative to the body tissue to which it is applied without causing trauma thereto, wherein each recessed area has a lengthwise dimension which exceeds a lengthwise dimension of each protuberance by a factor of at least two.

16. A hemostatic clip as recited in claim 15, wherein each of said projections are substantially convex in configuration.

17. A hemostatic clip as recited in claim 15, wherein each of said recessed areas are substantially concave in configuration.

18. A hemostatic clip as recited in claim 15, wherein said plurality of movement inhibiting structures on each of said leg portions are disposed equidistant from one another.

19. A hemostatic clip as recited in claim 15, further comprising means associated with an inner surface of said bail portion for permitting tissue exudation during application of said hemostatic clip.

20. A hemostatic clip as recited in claim 19, wherein said means for permitting tissue exudation comprises a pair of spaced apart notches each having a substantially V-shaped cross-sectional configuration.

21. A hemostatic clip as recited in claim 15, wherein said clip is fabricated from a material selected from the group consisting of stainless steel, tantalum, and titanium.

22. A hemostatic clip as recited in claim 15, wherein said pair of projections are generally spherical in configuration.

23. A hemostatic clip as recited in claim 15, wherein a lengthwise dimension of a recessed area is approximately twice as great as a lengthwise dimension of a projection.

24. A hemostatic clip as recited in claim 15, wherein said opposed side walls of each leg portion are arcuate in configuration.

25. A hemostatic clip for application to body tissue comprising:

a unitary clip body defining first and second opposed leg portions having respective proximal and distal ends with the proximal ends thereof connected by a bail portion, each of said first and second leg portions having a tissue contacting surface defined thereon which includes a plurality of structures, said structures on each of said leg portions including a pair of generally spherical protuberances and a pair of generally polyhedral recessed areas disposed equidistant from one another in an alternating arrangement, the distal-most structure provided on said first leg being a generally spherical protuberance and the distal-most structure provided on said second leg being a recessed area, such that said plurality of structures on said first leg are in juxtaposed alignment with said plurality of structures on said second leg, said spherical protuberances being dimensioned and configured to urge body tissue into said polyhedral recessed areas during the application of said hemostatic clip so as to inhibit dislocation of said clip with respect to the body tissue to which it is applied, wherein each polyhedral recessed area has a lengthwise dimension which exceeds the diameter of each spherical protuberances by a factor of at least two.

26. A hemostatic clip as recited in claim 25, further comprising means on an inner surface of said bail portion for permitting tissue exudation during application of said hemostatic clip.

27. A hemostatic clip as recited in claim 26, wherein said means for permitting tissue exudation comprises a pair of spaced apart notches each having a substantially V-shaped cross-sectional configuration.

28. A hemostatic clip as recited in claim 25, wherein said clip is fabricated from a material selected from the group consisting of stainless steel, tantalum, and titanium.

29. A hemostatic clip for application to body tissue comprising:

a deformable clip body defining first and second opposed leg portions and a connecting bail portion, each of said first and second leg portions having a tissue contacting surface defined thereon, said tissue contacting surface of said first leg portion having a plurality of spaced apart generally spherical protuberances provided thereon, said tissue contacting surface of said second leg portion having a plurality of spaced apart generally polyhedral recessed areas provided therein in juxtaposed alignment with said generally spherical protuberances, said protuberances being dimensioned and configured to urge body tissue into said recessed areas when said clip body is deformed and said opposed leg portions are brought into approximation by parallel closure, wherein each polyhedral recessed area has a lengthwise dimension which exceeds the diameter of each spherical protuberance by a factor of at least two.

* * * * *